(12) United States Patent
McGarity et al.

(10) Patent No.: US 7,473,255 B2
(45) Date of Patent: Jan. 6, 2009

(54) TRANSBUCCAL PLATE HOLDING CANNULA

(75) Inventors: Owen Carlos McGarity, Swarthmore, PA (US); Bryan James Griffiths, Coatesville, PA (US); Paul Christopher Ciccone, Lincoln University, PA (US); Ross Jonathan Hamel, West Chester, PA (US); Dana Joseph Coombs, Harleysville, PA (US); Robert Joseph Chilton, III, Quakertown, PA (US)

(73) Assignee: Synthes (U.S.A.), West Chester, PA (US)

( * ) Notice: Subject to any disclaimer, the term of this patent is extended or adjusted under 35 U.S.C. 154(b) by 359 days.

(21) Appl. No.: 11/349,559

(22) Filed: Feb. 8, 2006

(65) Prior Publication Data

US 2007/0213726 A1    Sep. 13, 2007

(51) Int. Cl.
*A61B 17/56* (2006.01)
(52) U.S. Cl. .................................... 606/86 B
(58) Field of Classification Search .................... 606/86, 606/110, 113, 114, 127, 86 R, 86 A, 86 B, 606/99, 102–105.5, 91, 101; 623/17.17, 623/17.18
See application file for complete search history.

(56) References Cited

U.S. PATENT DOCUMENTS

| | | | | |
|---|---|---|---|---|
| 2,549,731 A | * | 4/1951 | Wattley | 439/482 |
| 2,631,584 A | * | 3/1953 | Purificato | 606/68 |
| 2,933,114 A | | 4/1960 | Bystrom | 81/453 |
| 5,423,826 A | | 6/1995 | Coates et al. | |
| 5,667,513 A | * | 9/1997 | Torrie et al. | 606/104 |
| 5,755,721 A | | 5/1998 | Hearn | 606/96 |
| 5,782,747 A | * | 7/1998 | Zimmon | 600/104 |
| 5,782,830 A | * | 7/1998 | Farris | 606/99 |
| 6,319,257 B1 | * | 11/2001 | Carignan et al. | 606/99 |
| 6,436,103 B1 | | 8/2002 | Suddaby | 606/96 |
| 6,648,888 B1 | | 11/2003 | Shluzas | 606/61 |
| RE38,684 E | | 1/2005 | Cesarone | 606/69 |
| 6,916,323 B2 | * | 7/2005 | Kitchens | 606/86 |
| 7,001,333 B2 | * | 2/2006 | Hamel et al. | 600/242 |
| 7,357,804 B2 | * | 4/2008 | Binder et al. | 606/96 |
| 2004/0097937 A1 | | 5/2004 | Pike et al. | |
| 2005/0038444 A1 | | 2/2005 | Binder, Jr. et al. | 606/96 |
| 2005/0137606 A1 | | 6/2005 | Binder, Jr. et al. | 606/96 |
| 2006/0036254 A1 | * | 2/2006 | Lim | 606/86 |

FOREIGN PATENT DOCUMENTS

WO    03/015650 A1    2/2003

* cited by examiner

*Primary Examiner*—Eduardo C Robert
*Assistant Examiner*—Ellen Rust
(74) *Attorney, Agent, or Firm*—Woodcock Washburn LLP

(57) ABSTRACT

The present invention relates to a transbuccal plate holding cannula used in osteofixation procedures. The transbuccal plate holding cannula of the present invention can be releasibly secured to a bone plate such that tools and fasteners may be passed through the plate holding cannula in order to secure the bone plate to a bone.

20 Claims, 14 Drawing Sheets

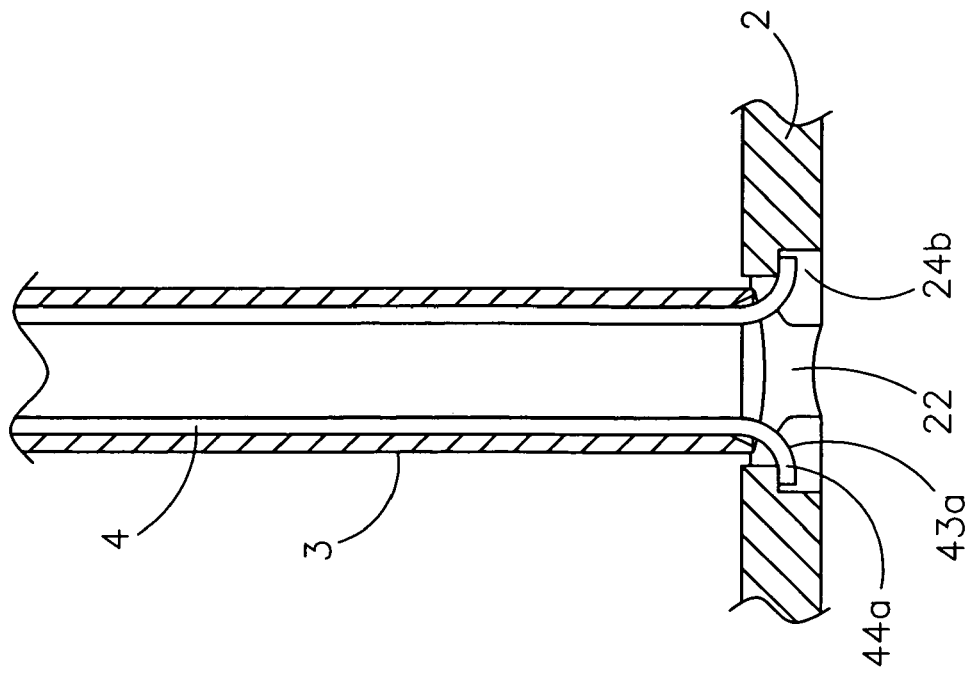
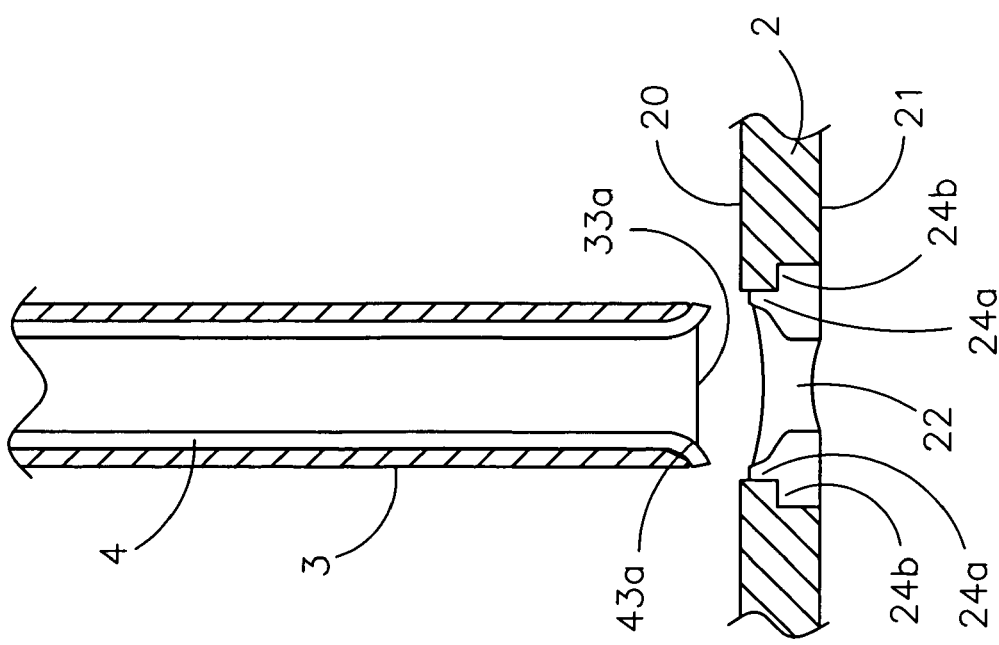

TRANSBUCCAL PLATE HOLDING CANNULA

TECHNOLOGY FIELD

Generally, the invention relates to instrumentation for osteofixation. More specifically, the invention relates to a transbuccal plate holding cannula.

BACKGROUND

The use of plates for osteofixation is well known. Plates are used to stabilize, mend, or align a patient's bone. Fasteners such as screws are driven through holes in the plate to secure the plate to the bone. The bone often needs to be drilled to allow the screws to be properly secured. The drilling is done through the holes in the plate to ensure proper alignment of the plate on the bone. Accurate alignment of the holes in the plate and the holes drilled in the bone is crucial to properly affix the plate to the bone. Thus, the plate must be maintained at a specific position on the bone while a hole is drilled and a screw is driven into the bone.

In order to accomplish the bone drilling, a drill guide is employed to ensure proper alignment of the plate hole with the hole drilled in the bone. In some cases, due to limited access, it is necessary to introduce drills and screws through a small incision in the soft tissues covering the site of osteofixation. A cannula is inserted into the soft tissue incision to ensure the opening is maintained, to provide access to the bone for drills and screws, and to provide protection for the surrounding soft tissue. Current cannula systems allow for passage of drill guides, drills, screwdrivers, and screws through a cannula that must be placed and held in alignment with the holes in the plate. Alignment of such cannula systems is accomplished by providing complementary geometry on the plate and the tip of the cannula. This method of alignment, however, requires constant axial pressure on the plate and is difficult to maintain. Relying on axial pressure for alignment makes it particularly difficult to manipulate the plate intraorally in maxillofacial surgery. Releasing axial pressure on the plate can cause the cannula and the plate to become misaligned with respect to the hole being drilled in the bone.

SUMMARY

The invention provides an instrument that securely holds a plate and allows the passage of tools and fasteners, such as drills and screws, through the instrument to secure the plate to a bone. The instrument allows a user to hold and manipulate a plate while drilling and screwing the plate to a bone without having to maintain constant axial pressure on the plate.

According to a preferred embodiment of the invention, the instrument comprises a tubular member and a tubular inner sleeve disposed telescopically within a central passageway in the tubular member. Preferably, the front end of the tubular member is made to self align with the plate by providing matching chamfered edges on the tubular member and holes in the plate. When the front end of the tubular member is aligned with a hole in the plate, the instrument can engage and hold the plate.

The inner sleeve has fingers extending from its front end. In one embodiment, the fingers are bent such that they extend radially outward and longitudinally forward from the front end of the inner sleeve. Further, the fingers have tips on their forward ends that are bent radially inward and transverse to the fingers.

According to a preferred embodiment, the inner sleeve is slidably disposed within the tubular member such that the fingers extend radially outward and axially forward through longitudinal slots in the tubular member when the back end of the inner sleeve is pressed forward. When the back end of the inner sleeve is released, the inner sleeve can slide back and the fingers can retract. The tips of the fingers may engage recesses on an outer surface of the tubular member in order to secure the inner sleeve to the tubular member. In one embodiment, a spring inside the tubular member causes the inner sleeve to slide back. The fingers extend and retract to securely engage the outer periphery of the plate while drills and screws are introduced through the inner sleeve. Once the instrument has engaged the plate, drills and screws can be introduced through the inner sleeve to secure the plate to the bone.

According to another aspect of the invention, the rear surface of the bone plate has recesses formed on the periphery of the plate close to the plate holes to further facilitate engagement of the plate by the fingers. The recesses on the back surface of the plate allow the plate holding instrument to position the plate substantially flush against the bone while the plate is being secured to the bone and allow the fingers to freely disengage after the plate has been secured to the bone.

According to another aspect of the invention, a rod is provided to be slidably inserted through a central passageway in the inner sleeve such that the front tip of the rod protrudes through a tip opening on the front end of the tubular member. Preferably, the front end of the rod tapers to a point so that when it protrudes through the tip opening of the tubular member, the front end of the tubular member can be more easily inserted and guided through an incision in the body.

In another embodiment, the fingers of the inner sleeve extend outwardly from the tubular member through the tip opening rather than through longitudinal slots on the front end of the tubular member. In this embodiment, the fingers are biased to expand radially outward as they are extended axially forward. Further, the tips of the fingers are bent radially outward to engage the inner periphery of the plate holes rather than the outer periphery of the plate while still allowing the passage of drills and screws through the inner sleeve.

According to another aspect of the invention, the bone plate has recesses formed adjacent to the plate holes to accept the fingers of the plate holding instrument. In one embodiment, the recesses extend alongside the plate holes and radially outward from the center of the plate holes. The recesses allow the fingers to engage the plate hole while still allowing drills and screws to freely pass through the plate holes.

Additional features and advantages of the invention will be made apparent from the following detailed description of illustrative embodiments that proceeds with reference to the accompanying drawings.

BRIEF DESCRIPTION OF THE DRAWINGS

The foregoing summary, as well as the following detailed description of the preferred embodiments, is better understood when read in conjunction with the appended drawings. For the purpose of illustrating the invention, there is shown in the drawings embodiments that are presently preferred, it being understood, however, that the invention is not limited to the specific methods and instrumentalities disclosed. In the drawings:

FIG. 13A shows a cross sectional view of the front end of another exemplary embodiment of the plate holding instrument and another exemplary embodiment of the bone plate; and FIG. 13B shows a cross sectional view of the front end of the exemplary plate holding instrument of FIG. 13A engaging the bone plate.

DETAILED DESCRIPTION OF ILLUSTRATIVE EMBODIMENTS

The present invention relates to instrumentation for osteofixation. More particularly, the invention relates to specially configured bone plates and instruments for holding bone plates during osteofixation procedures. A plate holding instrument 1 allows a user to securely hold a bone plate 2 to the bone while passing drills and screws through the bone plate 2.

Figure 1:
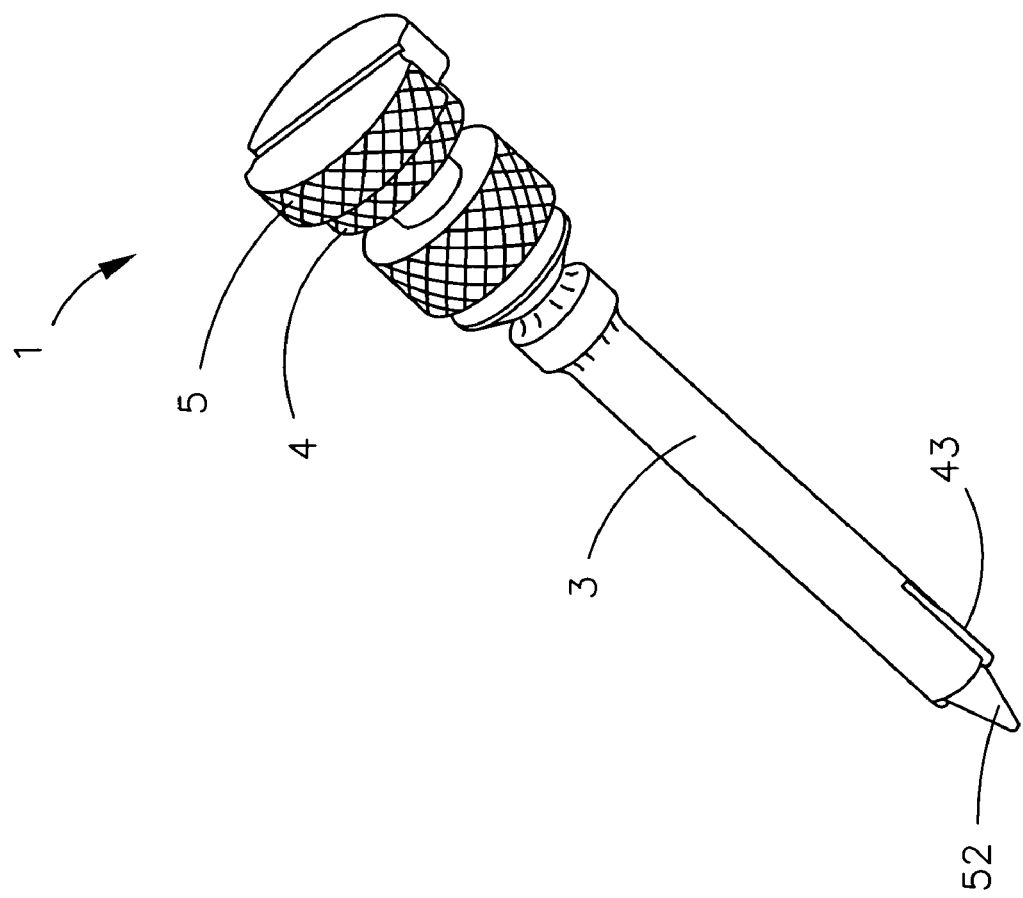
FIG. 1 shows an exemplary plate holding instrument.
Figure 2A:
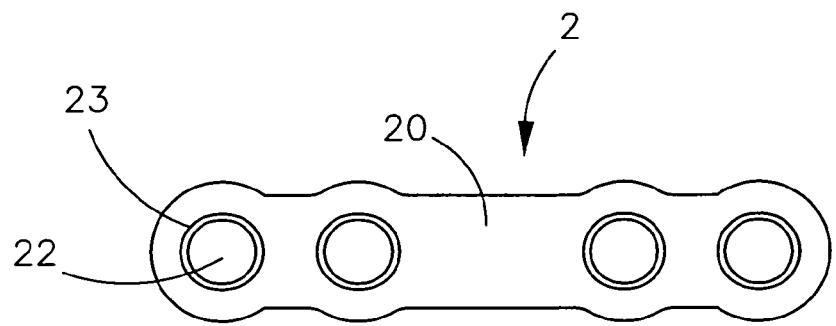
FIG. 2A shows a top view of an exemplary bone plate.
Figure 2B:
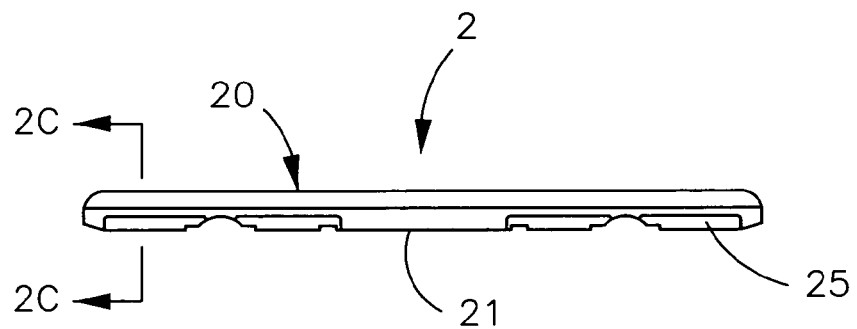
FIG. 2B shows a side view of an exemplary bone plate.
Figure 2C:
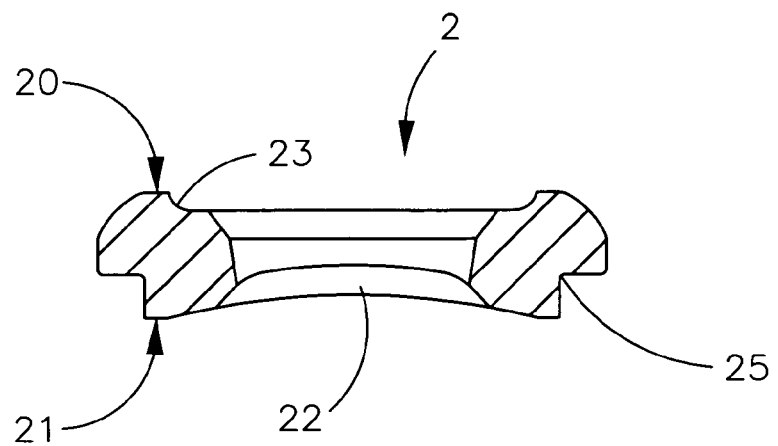
FIG. 2C shows a cross sectional view of an exemplary bone plate taken along sectional line 2C-2C of FIG. 2B.
Figure 6:
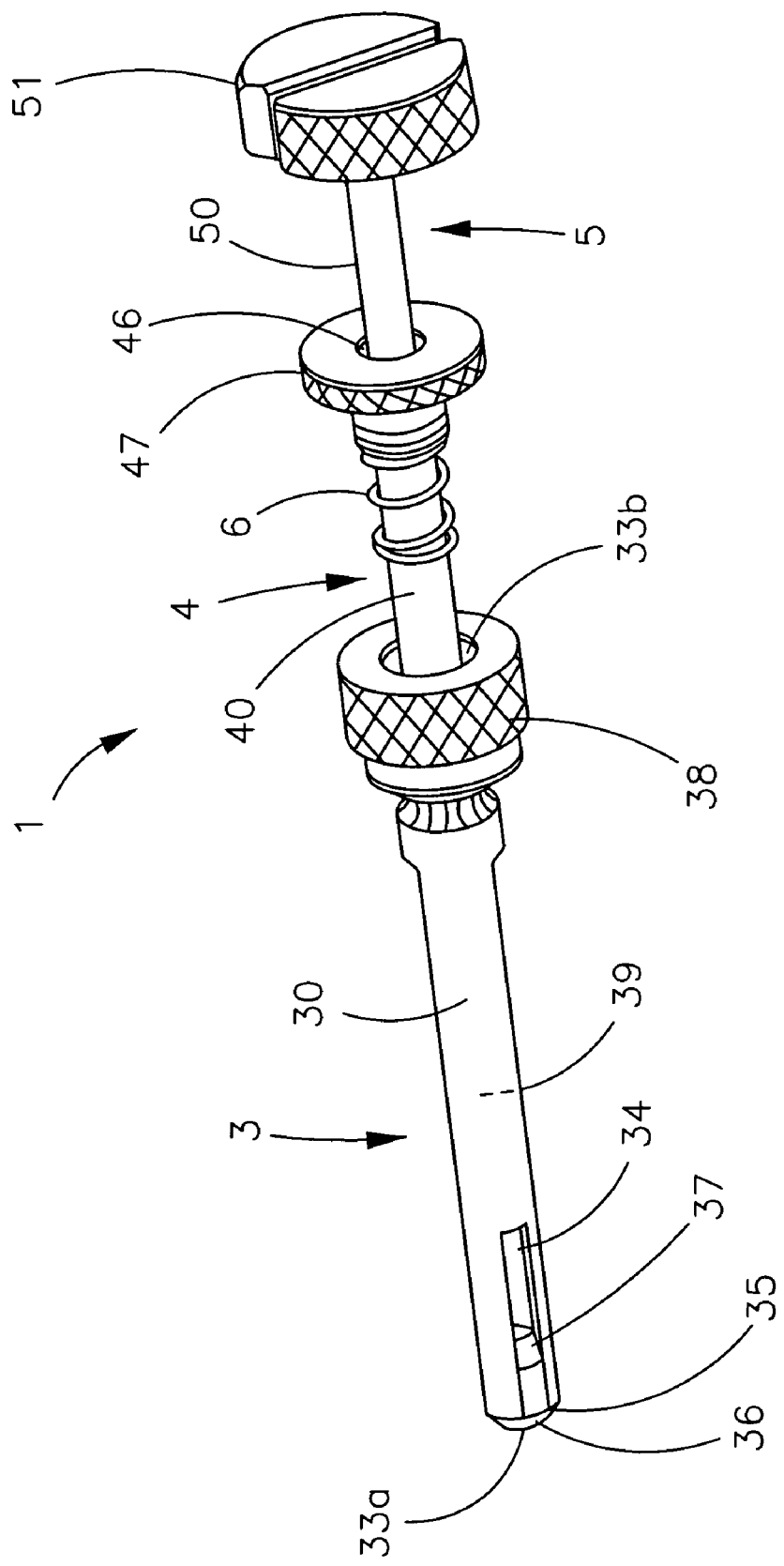
FIG. 6 shows a partially exploded view of an exemplary plate holding instrument.

In a preferred embodiment, the plate holding instrument 1 is a transbuccal plate holding cannula and the bone plate 2 is a mandible plate. A transbuccal plate holding cannula is used to rigidly capture a mandible plate intraorally, to manipulate plate placement, and to accurately pass drills and screws through the cannula into the plate. FIG. 1 shows a preferred embodiment of the plate holding instrument 1. FIGS. 2A-2C show a preferred embodiment of the bone plate 2. As shown in FIGS. 1 and 6, the plate holding instrument 1 includes a tubular member 3, an inner sleeve 4, and a rod 5.

As shown in FIGS. 2A-2C, a plate 2 includes a front surface 20, a rear surface 21, and at least one plate hole 22. The plate hole 22 extends through the plate 2 from the front surface 20 to the rear surface 21. Preferably, the periphery of the plate hole 22 on the front surface 20 of the plate 2 has a chamfered surface 23. In one embodiment, the outer periphery of the bone plate 2 on the rear surface 21 includes recesses 25.

Figure 3:
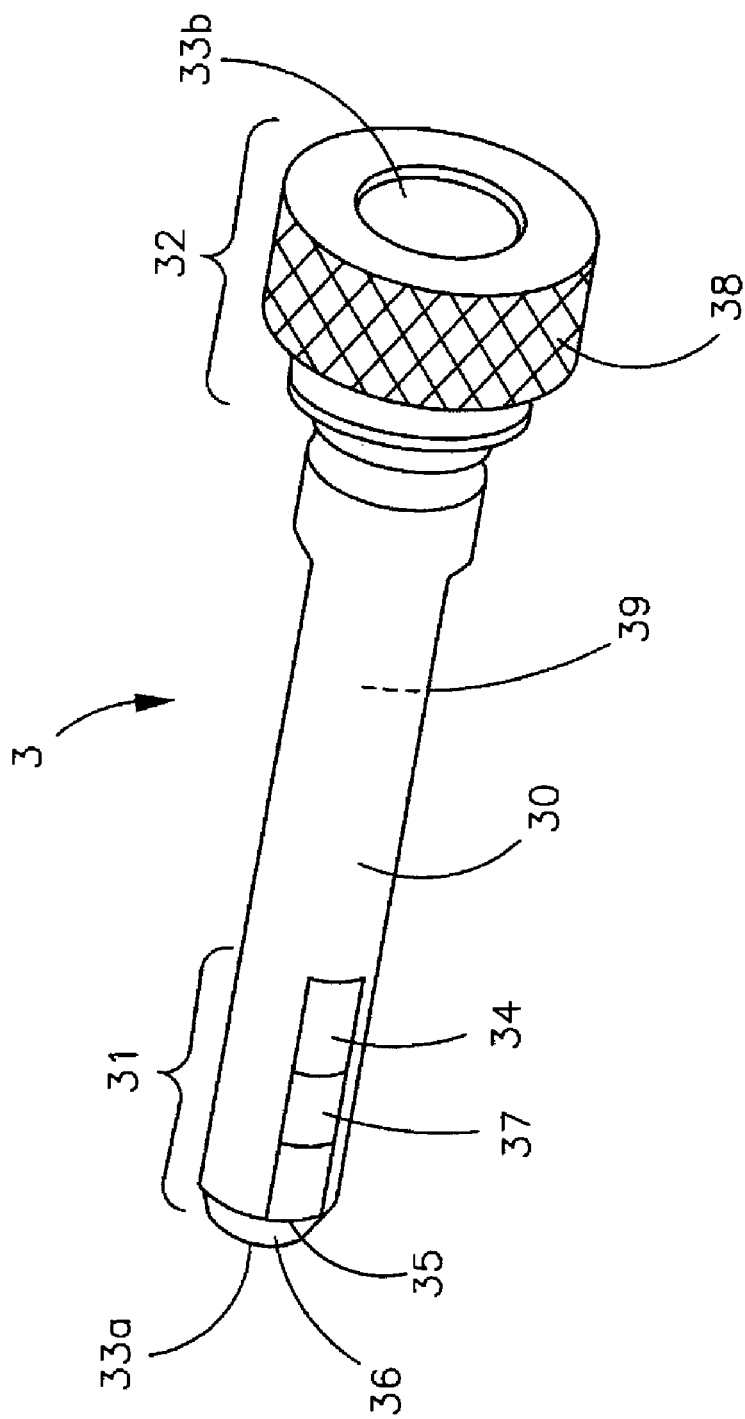
FIG. 3 shows an exemplary tubular member.

FIG. 3 shows an exemplary tubular member 3. As shown in FIG. 3, the tubular member 3 has a hollow, cylindrical body 30, a front end 31, and a rear end 32. The front end 31 has a tip opening 33a, at least two longitudinal slots 34 and at least two recesses 35 (only one is depicted) located around the circumference of the tubular member 3. Preferably, the outer surface 36 of the tip opening 33a is chamfered inwardly. As shown, the slots 34 extend from the tip opening 33a rearward along the longitudinal length of the body 30 of the tubular member 3. The forward surface of the slots 34 have ramps 37 that slope radially outward moving forward from the back end toward the front end. The recesses 35 are aligned with the slots 34 along the longitudinal axis of the tubular member 3 and are located longitudinally forward of the slots 34. The recesses 35 extend to the tip of the front end 31 of the tubular member 3. The rear end 32 of the tubular member 3 has an annular flange 38 and a rear opening 33b. A passageway 39 connects the tip opening 33a on the front end of the tubular member 3 to the rear opening 33b.

Figure 4A:
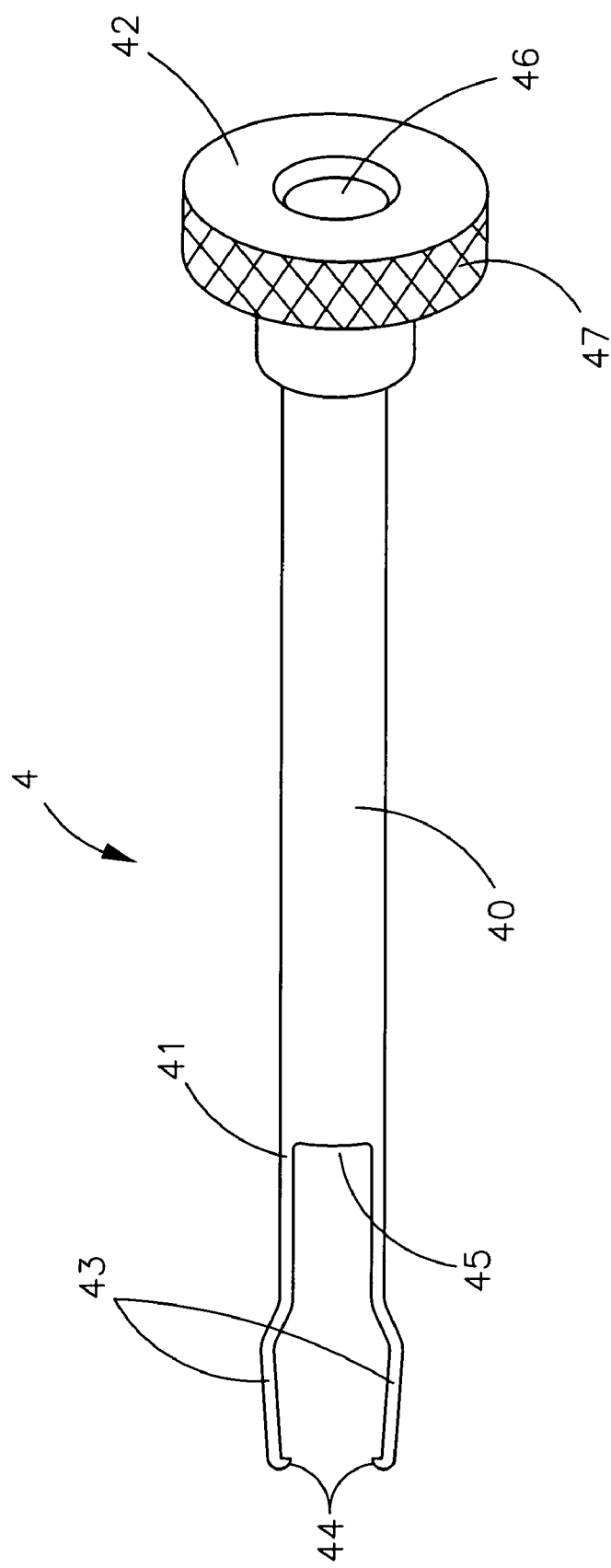
FIG. 4A shows an exemplary inner sleeve.
Figure 4B:
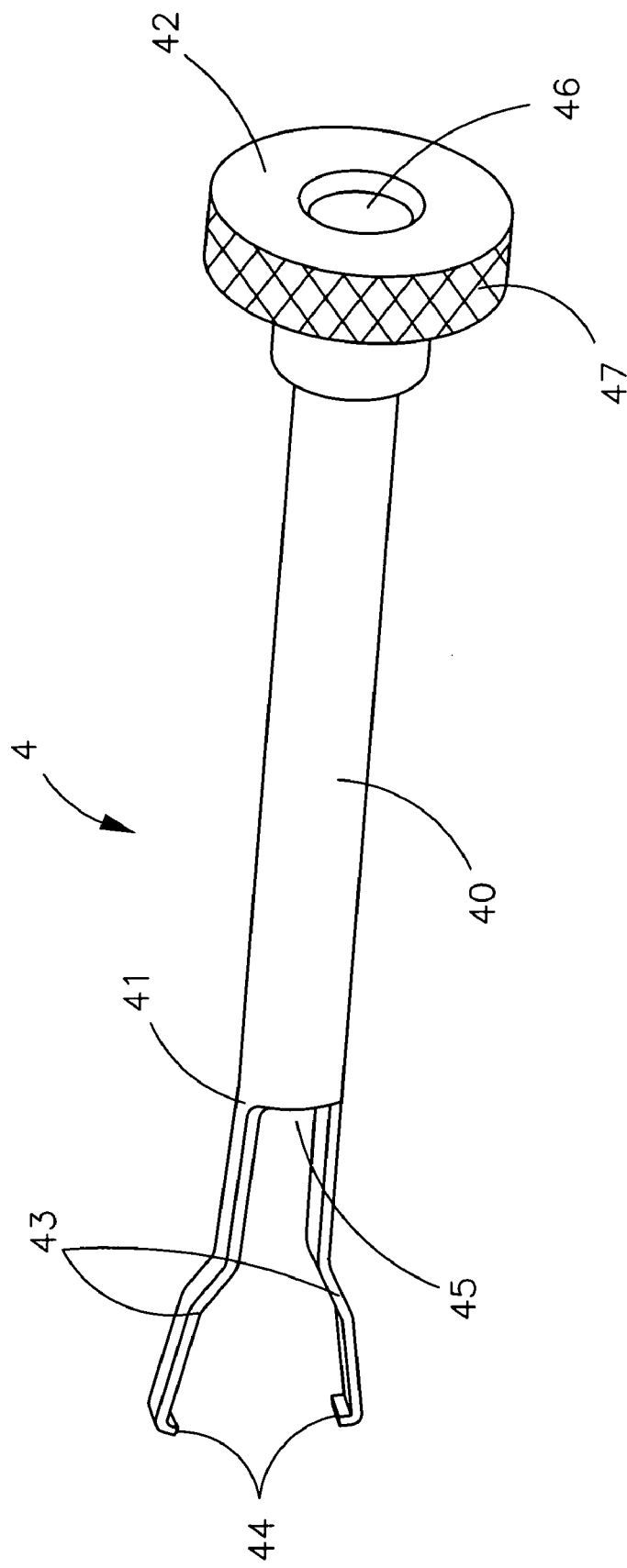
FIG. 4B shows another exemplary embodiment of the inner sleeve.

FIGS. 4A and 4B show exemplary inner sleeves 4. As shown in FIGS. 4A and 4B, the inner sleeve 4 has a hollow, cylindrical body 40, a front end 41, and a back end 42. There are at least two fingers 43 that extend from the front end 41 of the inner sleeve 4. The distal ends of the fingers 43 have tips 44. In a preferred embodiment, the tips 44 are bent radially inward, as shown in FIGS. 4A and 4B. The front end 41 of the inner sleeve 4 has a front opening 45 and the back end 42 of the inner sleeve 4 has a back opening 46. As shown in FIGS. 4A and 4B, the back end 42 of the inner sleeve 4 has an annular flange 47. In an embodiment shown in FIG. 4A, the fingers 43 are biased toward a closed position and are in substantial longitudinal alignment with the inner sleeve 4. In another embodiment shown in FIG. 4B, the fingers 43 are biased radially outward toward an open position.

Figure 5:
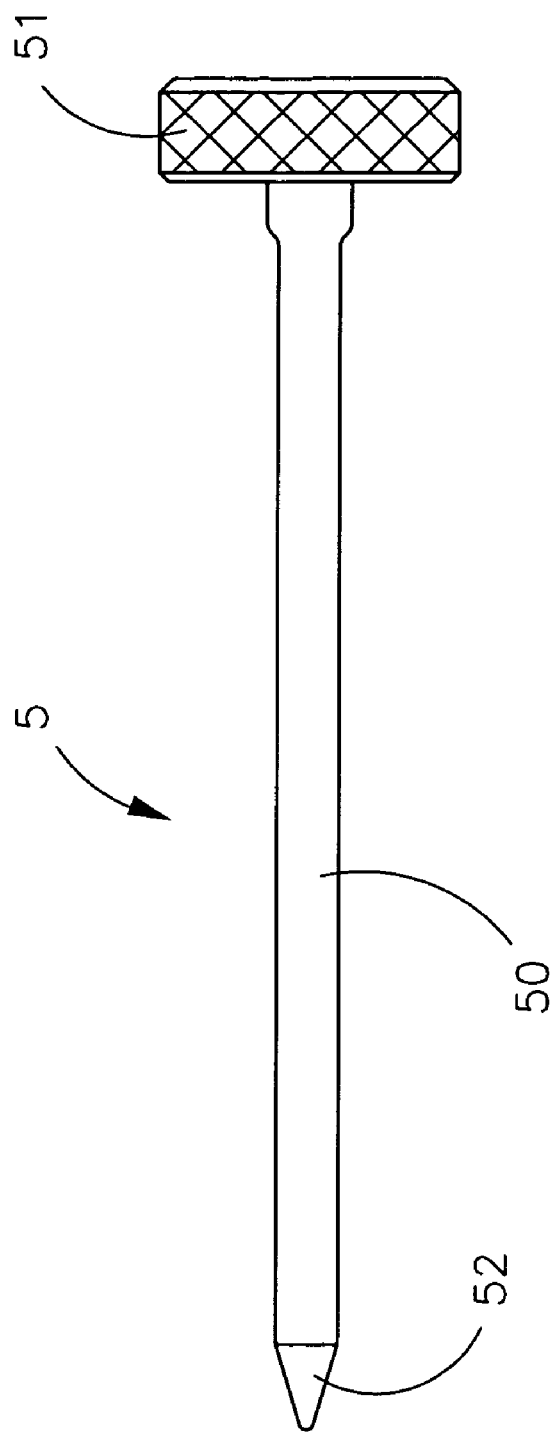
FIG. 5 shows an exemplary rod.

FIG. 5 shows and exemplary rod 5. Preferably, the rod 5 is an obturator. As shown in FIG. 5, the rod 5 has a body 50, an annular flange 51, and a tip 52. Preferably, the tip 52 of the rod 5 tapers to a blunt point.

Figure 7:
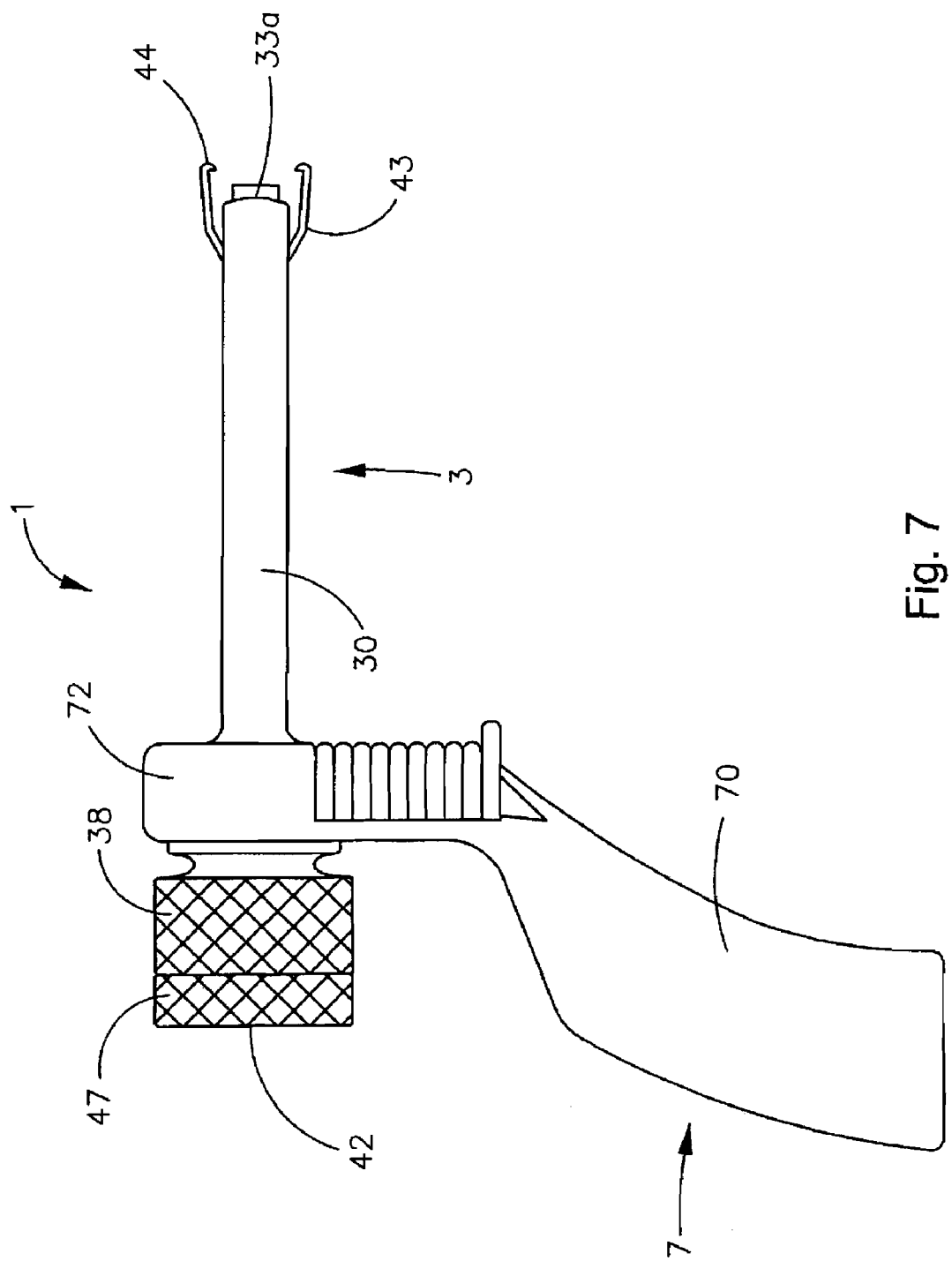
FIG. 7 shows an exemplary plate holding instrument having a handle and the fingers extended.
Figure 11:
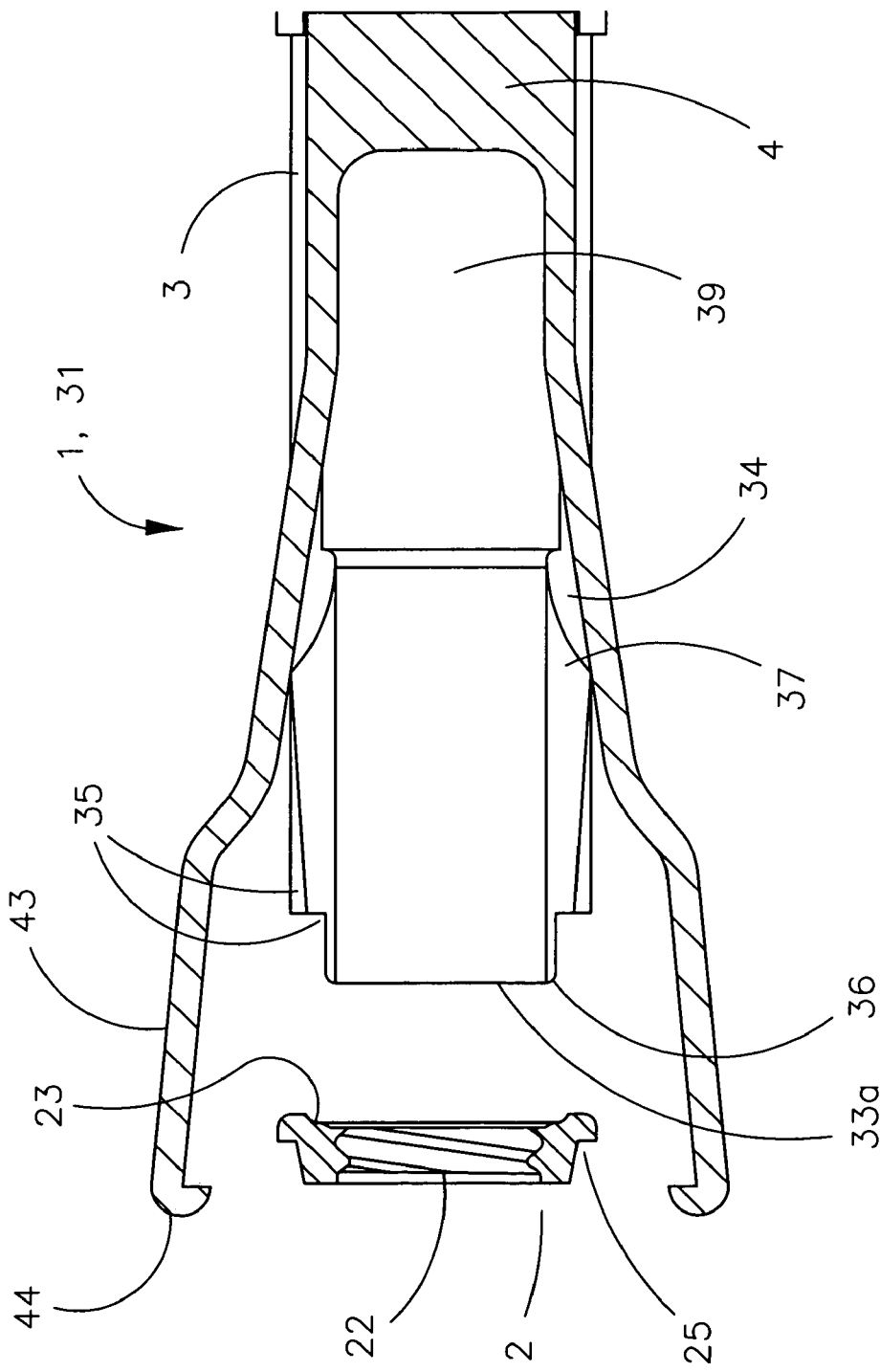
FIG. 11 shows a cross sectional view of the front end of an exemplary plate holding instrument with the fingers extended over an exemplary bone plate.

FIG. 6 shows a preferred assembly of the plate holding instrument 1. As shown in FIG. 6, the inner sleeve 4 is inserted through the rear opening 33b of the tubular member 3 and fits slidably therein. When the inner sleeve 4 is inserted into the tubular member 3 and slid forward, the fingers 43 protrude outwardly through the slots 34 of the tubular member 3, as shown in FIGS. 7 and 11. In the embodiment of FIG. 4A, the fingers 43 are biased closed and are forced open by the ramps 37 as the inner sleeve 4 is pressed forward in the tubular member 3. In the embodiment of FIG. 4B, the fingers 43 are biased open so that they extend axially outward through the slots 34 as the inner sleeve 4 is pressed forward in the tubular member 3.

Referring back to FIG. 6, a spring 6 is preferably located between the annular flange 47 of the inner sleeve 4 and the annular flange 38 of the tubular member 3 so that the inner sleeve 4 automatically slides back as it is released. In the embodiment of FIG. 4A, the fingers 43 are biased closed so that they move toward a closed position as the inner sleeve 4 slides back and off the ramps 37. In the embodiment of FIG. 4B, the fingers 43 are biased open and are forced closed by the tubular member 3 as the inner sleeve 4 slides back in to the tubular member 3. Ramps (not shown) may be provided on the back side of the slots to facilitate closing of the fingers. When the inner sleeve 4 slides back, the finger tips 44 engage the recesses 35 on the tubular member 3 and secure the inner sleeve 4 in the tubular member 3, thereby preventing the inner sleeve 4 from sliding further axially backward and out of the tubular member 3. Rod 5 is inserted into the back opening 46 of the inner sleeve 4, slid forward, and locked into the inner sleeve 4.

Figure 8:
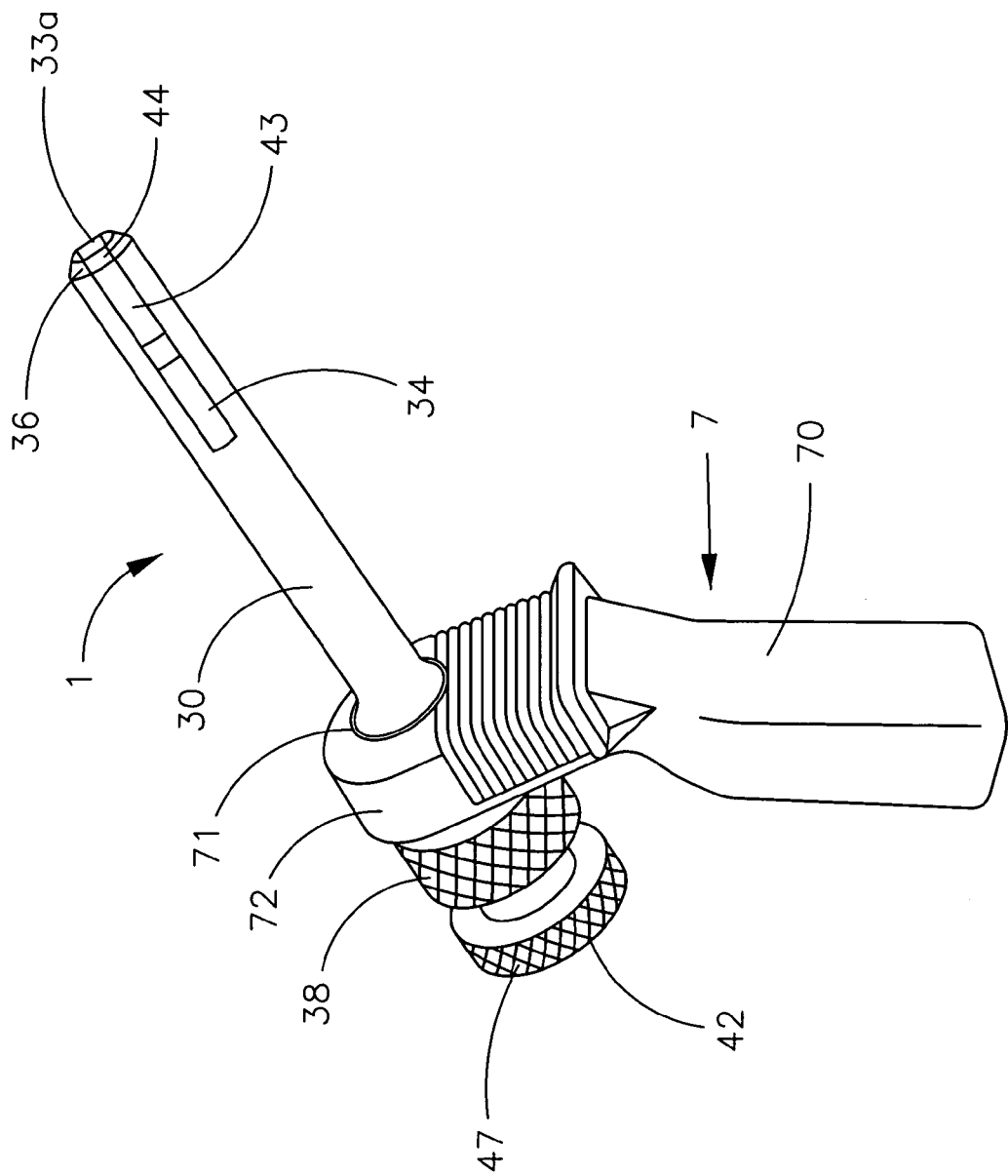
FIG. 8 shows an exemplary plate holding instrument having a handle and the fingers retracted.
Figure 9:
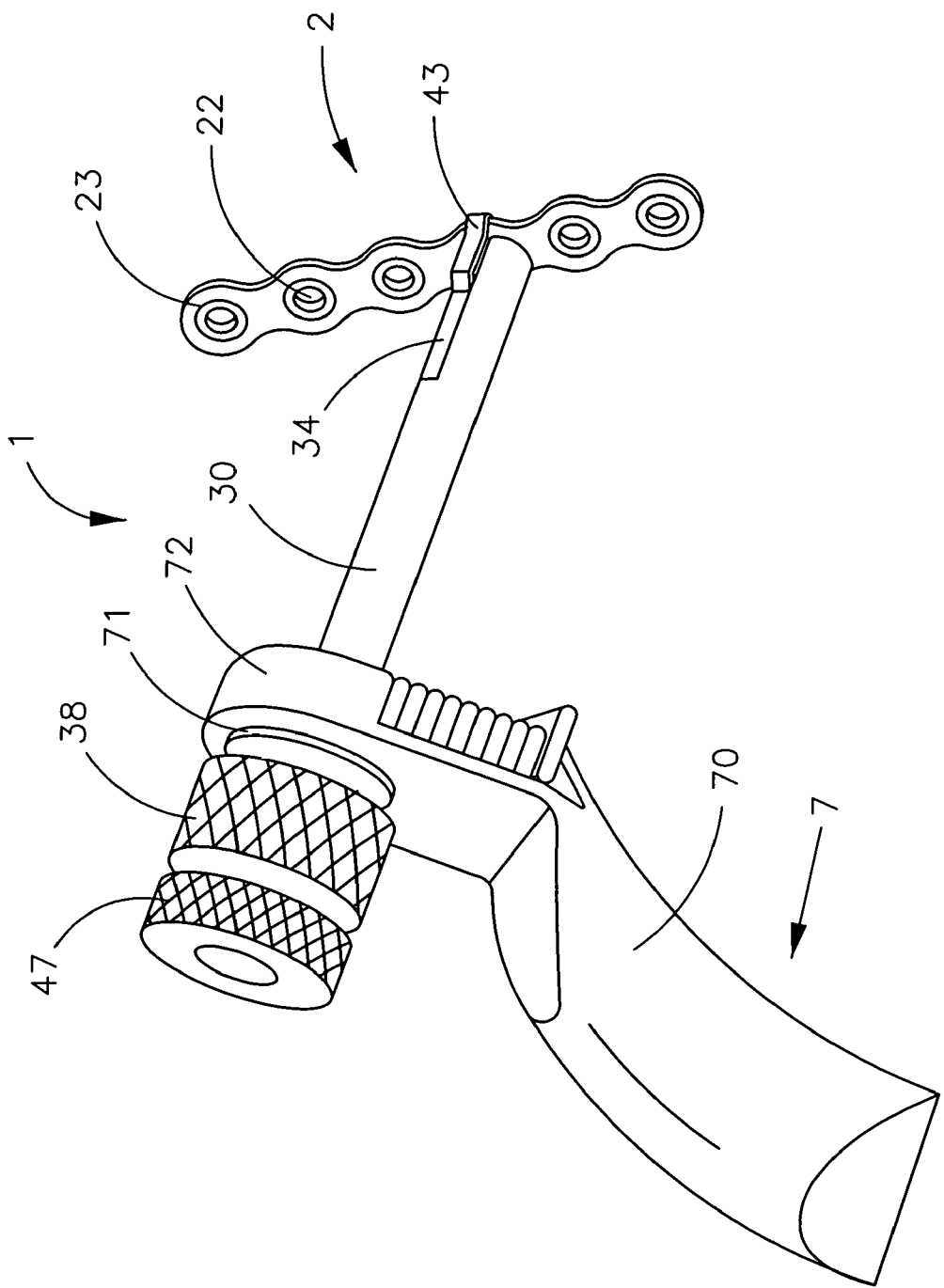
FIG. 9 shows an exemplary plate holding instrument having a handle and holding an exemplary bone plate.

As shown in FIGS. 7-9, a handle 7 can be attached to the body 30 of the tubular member 3. As shown, the handle 7 has a body 70 that has an annular opening 71 at an upper end 72. Preferably, the body 30 of the tubular member 3 is slid into the annular opening 71 of the handle 7 and is secured therein. For example, an internal spring loaded ball (not shown) and a corresponding mating recess (not shown) may be used to secure the tubular member 3 to the handle 7. The handle 7 facilitates manipulation of the plate holding instrument 1 and allows the plate holding instrument 1 to be manipulated with one hand.

According to another aspect of the invention, a handle 7 may include a ratchet gear mechanism (not shown) to actuate the forward movement of the inner sleeve 4 into the tubular member 3. The ratchet gear mechanism may include a lever arm having a distal end and a proximal end. The distal end of the lever arm may be in contact with the back end 42 of the inner sleeve 4, a central portion of the lever arm may be pivotally connected to the handle body 70, and the distal end may protrude through the handle body 70 to form a trigger, or be mechanically connected to a trigger mechanism. The trigger may be actuated to cause the distal end of the lever arm to move the inner sleeve 4 forward into the tubular member 3 in a controlled manner. The pivot point between the lever arm and the handle body 70 may incorporate a ratchet gear such that the forward movement of the distal end of the lever arm and the back end 42 of the inner sleeve 4 toward the tubular member 3 may be maintained. Further, a release mechanism may be employed to disengage the ratchet gear and allow the distal end of the lever arm and the back end 42 of the inner sleeve 4 to move back away from the tubular member 3.

As shown in FIG. 7, when the back end 42 of the inner sleeve 4 is pressed forward into the tubular member 3, the fingers 43 extend axially forward and radially outward through the slots 34 (not shown) of the tubular member 3. Referring to the embodiment of FIG. 11, the slots 34 have ramps 37 that force the fingers 43, which in one embodiment shown in FIG. 4A are biased closed, to expand radially outward through the slots as the inner sleeve 4 is pressed axially forward. Alternatively, if the fingers 43 are biased open, as shown in the embodiment illustrated in FIG. 4B, ramps are not required and the slots 34 allow the fingers to extend axially outward as the inner sleeve 4 is pressed forward in the tubular member 3. As shown in FIG. 11, the radial expansion of the fingers 43 allows the fingers 43 to extend over and around the outer periphery of a bone plate 2.

Figure 12:
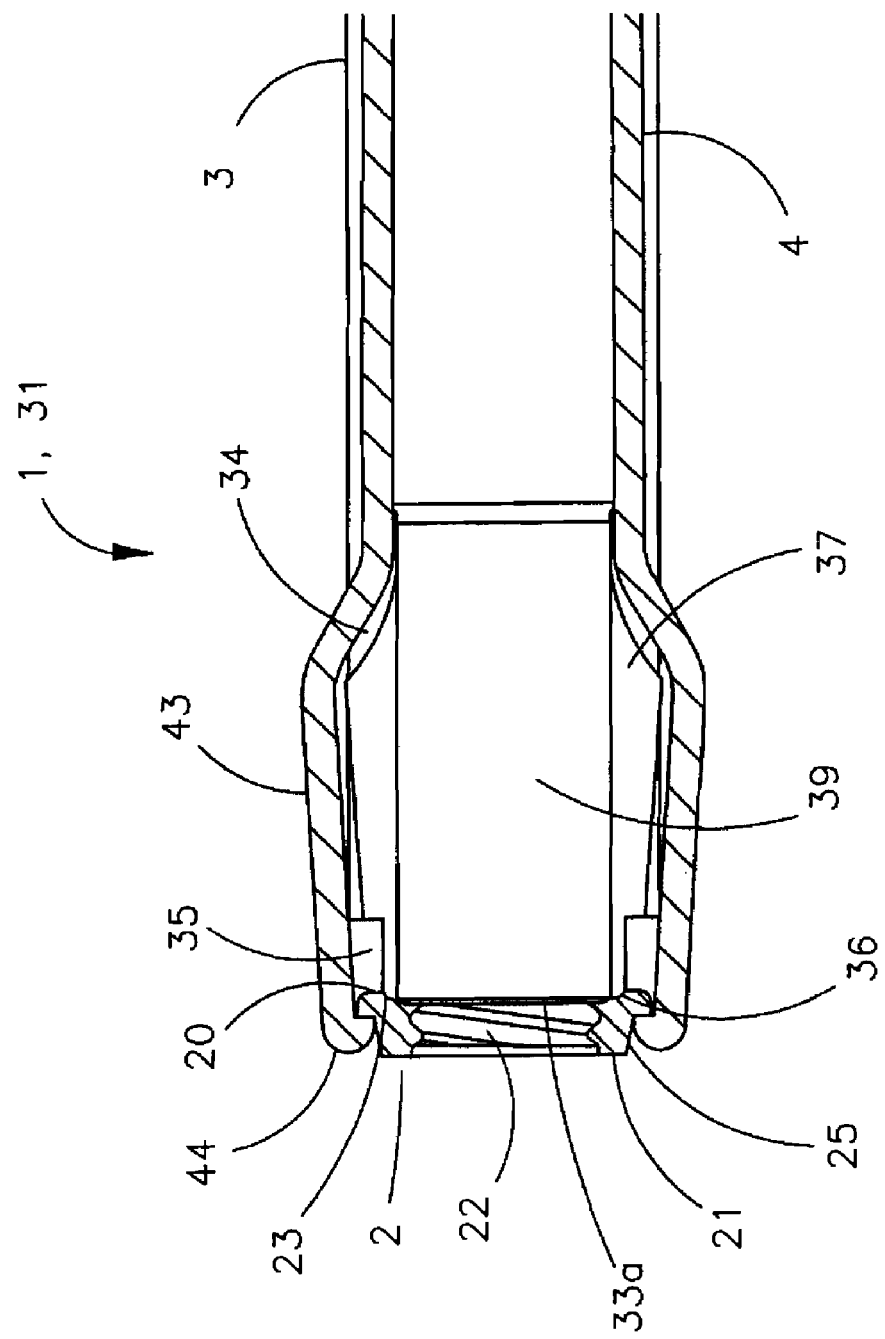
FIG. 12 shows a cross sectional view of the front end of an exemplary plate holding instrument engaging an exemplary bone plate.

As shown in FIG. 8, when the back end 42 of the inner sleeve is released and moved axially backward, the fingers 43 retract inwardly into the tubular member 3. Referring to FIG. 12, the retraction of the fingers 43 engages the outer periphery of a bone plate 2. According to another aspect of the invention, referring to FIG. 10, when the fingers 43 are retracted without engaging a plate 2, the finger tips 44 engage the recesses 35 on the tubular member 3, and the fingers 43 rest flush against the outer surface of the tubular member 3. The recesses 35 help prevent the fingers 43 from snagging tissue as the instrument 1 moves through incisions in the body.

A preferred method for using the devices of the present invention can be described with reference to FIGS. 10-12, which show a preferred embodiment of the plate holding instrument 1 in operation. First, a bone plate 2 is introduced into a patient's body at the site of desired osteofixation. Then, the plate holding instrument 1 is introduced into the body to manipulate the bone plate 2 and facilitate the fixation of the plate 2 to the bone.

Figure 10:
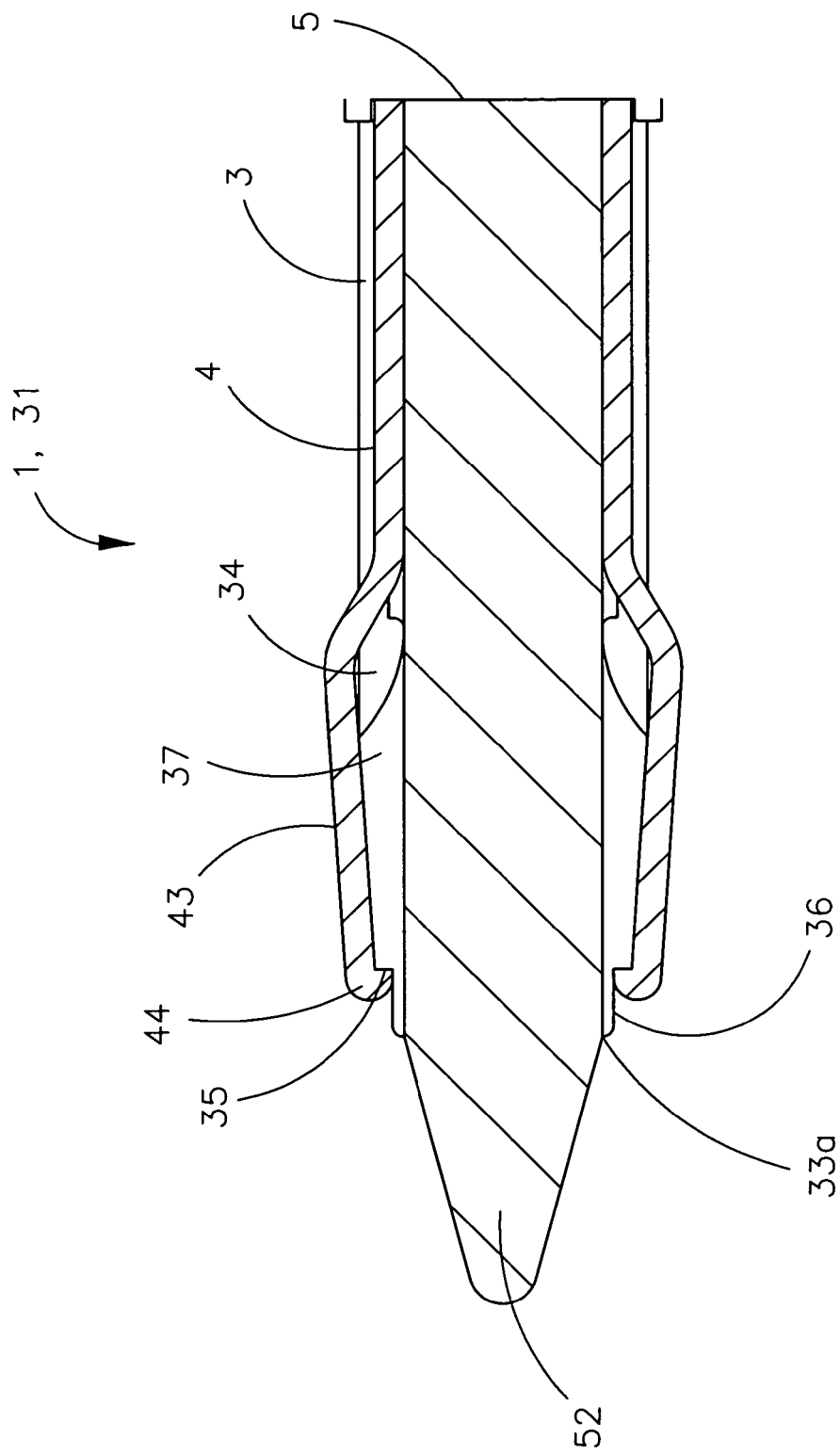
FIG. 10 shows a cross sectional view of the front end of an exemplary plate holding instrument.

As shown in FIG. 10, a rod 5 is inserted through the inner sleeve 4, the tip 52 of the rod 5 protrudes through the tip opening 33a of the tubular member 3. The protruding tip 52 of the rod 5 gives the plate holding instrument 1 a tapered front end that is easier to insert and guide through an incision in the body. Once plate holding instrument 1 is properly positioned within the incision, the rod 5 may be removed from the plate holding instrument 1.

Referring to FIG. 11, when a desired plate hole 22 is located, the back end 42 (not shown) of the inner sleeve 4 is pressed forward to extend the fingers 43 and engage the outer periphery of the bone plate 2. When the back end 42 (not shown) of the inner sleeve 4 is released, the inner sleeve 4 can slide back and the fingers 43 can retract. In one embodiment as shown in FIG. 6, a spring 5 is located between the annular flange 47 of the inner sleeve 4 and the annular flange 38 of the tubular member 3 so that the inner sleeve 4 slides back and the fingers 43 retract automatically when the back end 42 of the inner sleeve 4 is released. Further, the use of spring 5 to retract the inner sleeve 4 helps to positively maintain engagement of the plate 2 with the fingers 43.

Referring to FIG. 12, as the fingers 43 retract, the tips 44 of the fingers 43 engage recessed portions 25 on the rear surface 21 of the plate 2, and the front surface 20 of the plate 2 is moved against the front end 31 of the tubular member 3. The tip opening 33a of the tubular member 3 is brought into contact with the plate 2 such that the chamfered outer surface 36 of the tip opening 33a rests against the chamfered surface 23 around the periphery of the plate hole 22. When the plate holding instrument 1 is secured to the bone plate 2, drills and screws, for example, can be passed through the inner sleeve 4 to secure the bone plate 2 to the bone.

In another embodiment, shown in FIGS. 13A and 13B, the fingers 43a of the inner sleeve 4 engage the plate 2 through the plate holes 22 at recesses 24. Preferably, the bone plate 2 includes recesses 24 proximate the plate holes 22 and the fingers 43a extend into the recesses 24 to engage the plate 2. As shown, the bone plate 2 has a front surface 20, a rear surface 21, and at least one plate hole 22. The plate hole 22 extends through the plate 2 from the front surface 20 to the rear surface 21. As shown, recess 24 includes a first portion 24a and second portion 24b. The first portion 24a of the recess 24 is formed on the front surface 20 of the plate 2 and extends through the plate to the rear surface 21. The second portion 24b of the recess 24 is located adjacent to the rear surface 21 of the plate hole 22 and extends axially outward from a center of the plate hole 22. As shown, recess 24 extends generally radially outward from the front surface 20 to the rear surface 21.

In this embodiment, as shown in FIGS. 13A and 13B, the fingers 43a of the inner sleeve 4 extend longitudinally and radially outward from the tubular member 3 through the tip opening 33a. Preferably, the fingers 43a are curved outwardly so that they expand radially outward as they are extended past the end 33a. Further, the tips 44a of the fingers 43a are preferably bent radially outward to engage the recesses 24 adjacent to the plate holes 22 as the fingers 43a extend and expand into the bone plate 2.

In operation, the plate holding instrument 1 of FIGS. 13A and 13B is brought into contact with the plate 2. The tip opening 33a of the tubular member 3 contacts the periphery of the plate hole 22. The back end 42 of the inner sleeve 4 is pressed forward and the fingers 43a extend longitudinally and radially outward through the tip opening 33a of the tubular member 3. When the back end 42 of the inner sleeve 4 is pressed forward, the fingers 43a extend and expand and the tips 44a of the fingers 43a engage the recesses 24 to secure the plate 2. In this embodiment, drills and screws may be introduced to the bone plate 2 through the inner sleeve 4 while the inner sleeve 4 is pressed forward and the fingers 43a are securing the bone plate 2. When the back end 42 of the inner sleeve 4 is released, the fingers 43a retract and the plate holding instrument 1 disengages the bone plate 2.

While systems and methods have been described and illustrated with reference to specific embodiments, those skilled in the art will recognize that modification and variations may be made without departing from the principles described above and set forth in the following claims. Accordingly, reference should be made to the following claims as describing the scope of disclosed embodiments.

What is claimed:

1. An apparatus for holding a bone plate comprising:
a tubular member comprising:
a cylindrical body having a front end and a rear end;
a tip opening in said front end;
a rear opening in said rear end;
a passageway in said body extending from said tip opening to said rear opening;
at least two longitudinal slots disposed at said front end of said cylindrical body and around a circumference of said front end of said cylindrical body and extending axially rearward from said front end, at least a portion of said slots extending through said cylindrical body such that said slots form an opening to said passageway;
a flange disposed around said rear opening;
an inner sleeve being slideably disposed inside said passageway of said tubular member, said inner sleeve comprising:
a front end;
a back end; and
a flange disposed around said back end;
at least two substantially longitudinal fingers extending from said front end of said inner sleeve, said fingers being aligned with said longitudinal slots in said front end of said tubular member;
whereby said fingers extend axially forward and radially outward as said inner sleeve slides forward in said tubular member, and wherein said fingers retract axially rearward and radially inward as said inner sleeve slides backward in said tubular member; and
tips being formed at a distal end of said fingers and bent radially inward.

2. The apparatus of claim 1, wherein said tips engage said outer periphery of said bone plate against said front end of said tubular member as said fingers retract.

3. The apparatus of claim 1 further comprising a spring being disposed around said inner sleeve, between said flange of said tubular member and said flange of said inner sleeve.

4. The apparatus of claim 1, wherein said slots further comprise ramps, wherein said ramps slope radially outward in a longitudinal direction from said back end toward said front end.

5. The apparatus of claim 1, wherein said tubular member further comprises recesses located at said front end of said cylindrical body and on an outer surface of said cylindrical body such that said tips engage said recesses when said fingers are in a retracted position.

6. The apparatus of claim 1, wherein said front end of said tubular member further comprises a chamfered edge around an outer surface of said tip opening.

7. The apparatus of claim 1, further comprising a rod, said rod comprising:
a body having a front end and a back end;
a tapered tip on said front end; and
a flange disposed around said back end;
wherein said rod is slideably inserted into a passageway extending through said inner sleeve such that said flange on said back end of said rod rests on said flange on said back end of said inner sleeve.

8. The apparatus of claim 1, further comprising a handle, said handle comprising an annular opening, wherein said tubular member is inserted through said annular opening and secured to said handle.

9. The apparatus of claim 8, further comprising a ratchet mechanism for actuating the forward, sliding movement of said inner sleeve relative to said tubular member.

10. An apparatus for holding a bone plate comprising:
(a) a tubular member comprising:
a body having a front end and a rear end;
a tip opening in said front end;
a rear opening in said rear end;
a passageway in said body extending from said tip opening to said rear opening;
at least two longitudinal slots disposed at said front end of said body and around a periphery of said front end of said body and extending longitudinally rearward from said front end, at least a portion of said slots extending through said body such that said slots form an opening to said passageway; and
a flange disposed around said rear opening; and
(b) an inner sleeve being slideably disposed inside said passageway of said tubular member, said inner sleeve comprising:
a front end;
a back end;
a flange disposed around said back end;
at least two substantially longitudinal fingers extending from said front end of said inner sleeve, said fingers being aligned with said longitudinal slots in said front end of said tubular member; and
finger tips being formed at a distal end of said fingers and bent radially inward;
whereby said fingers extend longitudinally forward and radially outward as said inner sleeve slides forward in said tubular member, and wherein said fingers retract longitudinally rearward and radially inward as said inner sleeve slides backward in said tubular member.

11. The apparatus of claim 10, wherein said finger tips engage said outer periphery of said bone plate against said front end of said tubular member as said fingers retract.

12. The apparatus of claim 10 further comprising a spring being disposed around said inner sleeve, between said flange of said tubular member and said flange of said inner sleeve.

13. The apparatus of claim 10, wherein said slots further comprise ramps, wherein said ramps slope radially outward in a longitudinal direction from said back end toward said front end.

14. The apparatus of claim 10, wherein said tubular member further comprises recesses on an outer surface at said front end of said body such that said tips engage said recesses when said fingers are in a retracted position.

15. The apparatus of claim 10, wherein said front end of said tubular member further comprises a chamfered edge around an outer surface of said tip opening.

16. The apparatus of claim 10, wherein said inner sleeve has an inner passageway, and the apparatus further comprises a rod, said rod comprising:
a body having a front end and a back end;
a tapered tip on said front end; and
a flange disposed around said back end;
wherein said rod is slideably inserted into said sleeve passageway such that said flange on said back end of said rod rests on said flange on said back end of said inner sleeve.

17. The apparatus of claim 10, further comprising a handle, said handle comprising an annular opening, wherein said tubular member is inserted through said annular opening and secured to said handle.

18. The apparatus of claim 17, further comprising a ratchet mechanism for actuating the forward, sliding movement of said inner sleeve relative to said tubular member.

19. The apparatus of claim 10 wherein said finger tips are biased open.

20. The apparatus of claim 10 wherein said finger tips are biased closed.

* * * * *